United States Patent [19]

Knoll et al.

[11] Patent Number: 4,919,662
[45] Date of Patent: Apr. 24, 1990

[54] HYDROGEL IMPLANT LENS CONSTRUCTION RECONFIGURED DEHYDRATED RE-HYDRATED IN SITU

[75] Inventors: Randall L. Knoll, Stillwater; Wilhelm Lewon, St. Paul; Ronald Ofstead, Maplewood, all of Minn.

[73] Assignee: Minnesota Mining and Manufacturing Company, St. Paul, Minn.

[21] Appl. No.: 245,407

[22] Filed: Sep. 16, 1988

[51] Int. Cl.⁵ ............................................. A61F 2/16
[52] U.S. Cl. ...................................................... 623/6
[58] Field of Search .......................... 623/6; 351/160 H

[56] References Cited

U.S. PATENT DOCUMENTS

| | | | |
|---|---|---|---|
| 4,122,556 | 10/1978 | Poler | 623/6 |
| 4,338,687 | 7/1982 | Rainin | 623/6 |
| 4,373,218 | 2/1983 | Schachar | 623/6 |
| 4,449,257 | 5/1984 | Koeniger | 623/6 |
| 4,466,705 | 8/1984 | Michelson | 350/418 |
| 4,528,325 | 7/1985 | Ofstead | 525/60 |
| 4,556,998 | 12/1985 | Siepser | 623/6 |
| 4,573,998 | 3/1986 | Mazzocco | 623/6 |
| 4,578,078 | 3/1986 | Arkell et al. | 623/6 |
| 4,618,649 | 10/1986 | Ofstead | 525/60 |
| 4,693,939 | 9/1987 | Ofstead | 428/421 |
| 4,694,037 | 9/1987 | Ofstead | 524/557 |
| 4,725,276 | 2/1988 | Bissonette | 623/6 |
| 4,725,277 | 2/1988 | Bissonette | 623/6 |
| 4,725,278 | 2/1988 | Shearing | 623/6 |
| 4,731,079 | 3/1988 | Stoy | 623/6 |
| 4,734,095 | 3/1988 | Siepser | 623/6 |
| 4,743,254 | 5/1988 | Davenport | 623/6 |
| 4,769,034 | 9/1988 | Poley | 623/6 |
| 4,771,089 | 9/1988 | Ofstead | 524/41 |
| 4,778,463 | 10/1988 | Hetland | 623/6 |
| 4,787,904 | 11/1988 | Severin et al. | 623/6 |
| 4,813,954 | 3/1989 | Siepser | 623/6 |

FOREIGN PATENT DOCUMENTS 00188110 7/1986 European Pat. Off. .
2180160A 3/1987 United Kingdom ................. 623/6

OTHER PUBLICATIONS

"Soft Intraocular Lenses", Allarakhia, Knoll and Lindstrom, J Cataract Refract Surg, vol. 13, Nov. 1987.

Primary Examiner—Ronald L. Frinks
Attorney, Agent, or Firm—Donald M. Sell; Walter N. Kirn; Dale A. Bjorkman

[57] ABSTRACT

This invention provides a new method of preparing intraocular lenses for implantation which comprises folding, stretching, rolling, compressing or otherwise reconfiguring the lens to reduce the profile of the lens in at least one dimension and dehydrating the lens in that shape. The thus prepared artificial intraocular lens may be surgically implanted in the eye through a small incision where it will be rehydrated in situ.

10 Claims, 2 Drawing Sheets

HYDROGEL IMPLANT LENS CONSTRUCTION RECONFIGURED DEHYDRATED RE-HYDRATED IN SITU

FIELD OF INVENTION

This invention relates to artificial intraocular lenses. Specifically, the invention relates to lenses, methods of preparing lenses and methods of using lenses which are relatively small in size for small incision insertion in the eye.

BACKGROUND OF THE INVENTION

Artificial intraocular lenses have been accepted as replacements for the human crystalline lens when medical conditions require such a replacement. Phacoemulsification surgical techniques now allow the surgeon to remove the natural lens through a very small incision in the ocular tissue, but the size of the replacement artificial intraocular lens has always required a larger incision to be made. Additionally, the size of the lens and particularly the extension of the haptic will at times make a placement of the entire lens within the capsular bag difficult.

A smaller sized artificial intraocular lens at the time of insertion would allow for a small corneal incision, affording the advantages of fewer occurrences of corneal astigmatism and faster healing. Also, a smaller incision for the anterior capsulotomy coupled with a miniaturized lens construction would allow for greater security of "in the bag" placement because there is more integrity of the bag.

Many efforts have been made in the past to provide an artificial intraocular lens which is capable of being implanted through a small incision. U.S. Pat. No. 4,373,218 to Schachar provides an intraocular lens which is a fluid expandable sac insertable in a collapsed condition and then filled with fluid.

U.S. Pat. No. 4,573,998 to Mazzocco discloses a method for compressing the lens and inserting it through a relatively small opening. Although insertion of the lens in a dry state is disclosed in column 13, line 25, this disclosure appears to view dehydration alone as a form of deformation, and not in conjunction with physical deformation. The reference does not teach the compression of the lens followed by dehydration in the compressed state.

U.S. Pat. No. 4,556,998 to Siepser discloses insertion of a dry lens which hydrates in the natural eye fluid. The lens is prepared from dry materials, so that dehydration is never required. No reconfiguration of the lens before insertion or preparation is taught.

U.S. Pat. No. 4,731,079 to Stoy discloses the reconfiguration and cooling of a lens, thereby freezing the lens in a particular configuration. The lens is allowed to reheat in the body where it returns to its original dimensions.

SUMMARY OF THE INVENTION

A method of reducing the cross-section or the length of an intraocular lens in at least one dimension has been discovered where a lens made of a hydrogel material having specifically required physical properties is reconfigured, thereby reducing the cross-section in at least one dimension and dehydrated in position so that it retains its reconfigured shape. Reconfiguration is achieved by folding, stretching, rolling, compressing or otherwise modifying the shape of the lens in order to reduce the effective cross-section in at least one dimension. The profile that this reconfigured intraocular lens presents is smaller in at least one dimension than current intraocular lenses available and enables insertion into the eye through a relatively smaller incision in the ocular tissue than was previously possible. Certain reconfigurations of the lens will reduce the total length of the lens, making it possible for the entire lens to be more readily placed inside the capsular bag.

Dehydration is achieved by any appropriate method, such as passing air or nitrogen over the lens, allowing the lens to air dry or placing the lens in a dry environment such as in the presence of a desiccant. The lens is surgically inserted in the ocular bag after removal of the natural lens and rehydrates gradually in the natural fluid present in the eye to an optically correct lens. This gradual rehydration and consequent expansion to a sufficient extent to provide stabilization in the eye takes place in a predictable period of time of approximately one to twenty minutes without the sudden recoil inherent in compressed elastomeric materials that could cause damage to the fragile tissues of the eye. The lens generally fully rehydrates to provide proper optics in about 24 hours.

BRIEF DESCRIPTION OF THE DRAWINGS

FIG. 8 shows the lens of FIG. 7 with two of the haptics folded in.

FIG. 9 shows the lens of FIG. 7 with all three haptics folded in.

DETAILED DESCRIPTION

This invention provides an artificial intraocular lens for implantation within the eye. This lens is prepared in a method comprising the steps of:

(a) providing an intraocular lens whose optic and/or supporting structure comprises at least a portion which has prescribed shape, dimension and physical characteristics such that it can be (i) folded, stretched, rolled, compressed or otherwise reconfigured to a configuration such that the profile of the lens is reduced in at least one dimension, (ii) dehydrated so that the lens will substantially retain the configuration which provides the reduced profile, (iii) inserted through a relatively small incision made in the ocular tissue and (iv) allowed to rehydrate by the natural fluid present in the eye and expand to provide an optically correct lens;

(b) folding, stretching, rolling, compressing or otherwise reconfiguring said lens to a configuration such that the profile of the lens is reduced in at least one dimension and;

(c) dehydrating said reconfigured lens so that the lens substantially retains the configuration which provides the reduced profile.

The lens provided by this method is then inserted through a relatively small incision made in the ocular tissue and allowed to rehydrate by the natural fluid present in the eye and expands to provide an optically correct lens. An optically correct lens according to this invention is a lens which is stabilized or fixated in the eye and which possesses proper optic properties.

Figure 1:
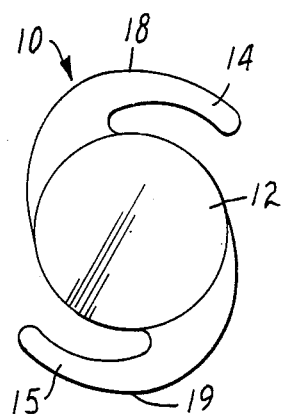
FIG. 1 shows an intraocular lens having C-shaped haptics made of the same material as the optic.

Referring to the drawings, FIG. 1 shows an intraocular lens 10 having an optic 12 and two opposingly located C-shaped haptics 14 and 15 made of the same hydrogel material as the optic 12.

Figure 2:
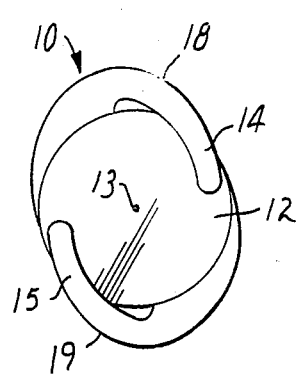
FIG. 2 shows the lens of FIG. 1 with the haptics compressed radially inward.

FIG. 2 shows the lens 10 after the haptics 14 and 15 have been compressed or drawn in a radially inward fashion to positions generally in a plane perpendicular to the visual axis 13 of the lens in front or in back of the optic 12, as defined by the position of the lens after insertion in the eye, in order to reduce the total distance between the radially outermost points of the haptics 18 and 19. Said haptics 14 and 15 are optimally compressed or drawn inwardly in such a manner that the haptics are not folded over or twisted in any way. The haptics in this step should travel in as direct a line as possible without rotation of the haptic relative to the optic, and will follow the same direct path upon rehydration. When following this technique of reconfiguration of the haptics, said radially outermost points 18 and 19 continue to be located on the radially outermost surface of the haptic. The possibility of damage to fragile ocular tissues is thereby reduced which could otherwise be caused by the sweeping out of an arc that would result if the haptics were simply folded over to the same position. The lens is then dehydrated so that the haptics 14 and 15 substantially retain this configuration and the lens will reduce in overall size. In the alternative, the lens may be partially dehydrated so that the haptics retain their reconfigured positions and the optic of the lens 12 may itself be reconfigured.

Figure 3:
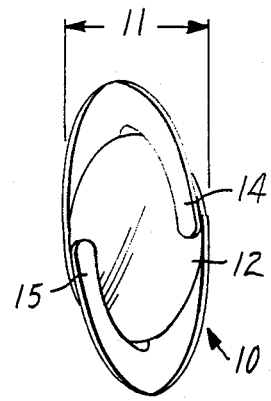
FIG. 3 shows the lens of FIG. 1 with the haptics compressed radially inward and the optic also reconfigured.

FIG. 3 shows the lens of FIG. 2 where the optic 12 has been reconfigured to present a smaller profile by reducing the width 11 of the lens. The optic of the lens may be reconfigured by compressing, folding, stretching or rolling the lens as will be later described.

Figure 4:
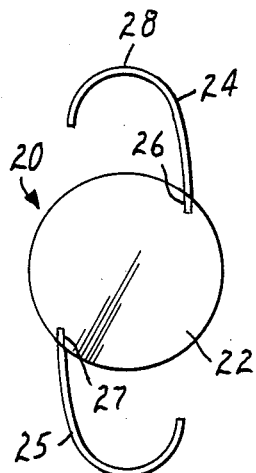
FIG. 4 shows an intraocular lens having J-shaped haptics made of a non-hydrogel material and an optic made of a hydrogel material.

FIG. 4 shows an intraocular lens 20 having two opposingly located J-shaped haptics 24 and 25 made from non-hydrogel material such as nylon, polyurethane, silicone, polyamide, polypropylene, polyimide, polyvinylidene fluoride and polyethylene and an optic 22 made of a hydrogel material. These haptics are optimally mounted according to the method disclosed in U.S. Ser. No. 168,374, filed Mar. 15, 1988, hereby incorporated by reference. Because of the relative rigidness of the haptic with respect to the optic materials, compression of the haptics 24 and 25 will result in a compression in the optic in the regions of attachment 26 and 27 of the haptic.

Figure 5:
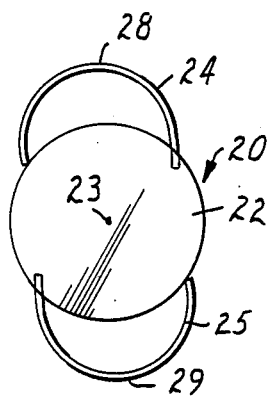
FIG. 5 shows the lens of FIG. 4 with the haptics compressed radially inward.

FIG. 5 shows the lens 20 after the haptics 24 and 25 have been compressed or drawn in a radially inward fashion to positions generally in a plane perpendicular to the visual axis 23 of the lens in front or in back of the optic 22 in order to reduce the total distance between the radially outermost points of the haptics 28 and 29. Said haptics 24 and 25 are optimally compressed or drawn inwardly in such a manner that the haptics are not folded over or twisted in any way. The haptics in this step should travel in as direct a line as possible without rotation of the haptic relative to the optic, and will follow the same direct path upon rehydration. When following this technique of reconfiguration of the haptics, said radially outermost points 28 and 29 continue to be located on the radially outermost surface of the haptic. The possibility of damage to fragile ocular tissues is thereby reduced which could otherwise be caused by the sweeping out of an arc that would result if the haptics were simply folded over to the same position. The lens is then dehydrated so that the haptics 24 and 25 substantially retain this configuration and the lens will reduce in overall size. In the alternative, the lens may be partially dehydrated so that the haptics retain their reconfigured positions and the optic of the lens 22 may itself be reconfigured.

Figure 6:
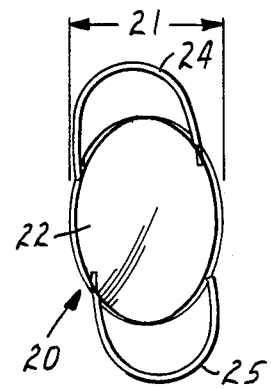
FIG. 6 shows the lens of FIG. 4 with the haptics compressed radially inward and the optic also compressed.

FIG. 6 shows the lens of FIG. 5 where the optic 22 has been reconfigured to present a smaller profile by reducing the width 21 of the lens. The optic of the lens may be reconfigured by compressing, folding, stretching or rolling the lens as will be later described.

Figure 7:
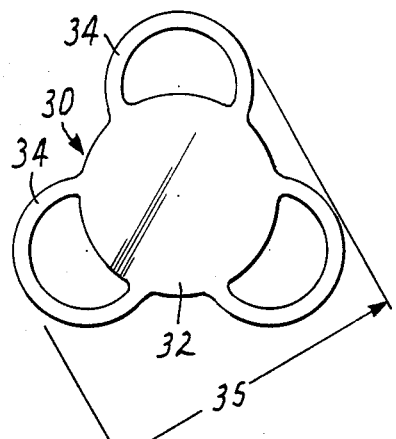
FIG. 7 shows an intraocular lens with three haptics in the 3-planar configuration.
Figure 8:
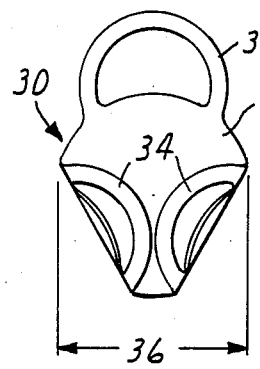
Figure 9:
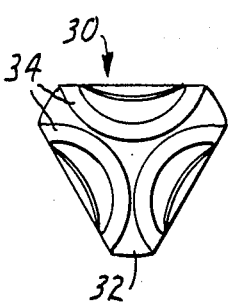

FIG. 7 shows an intraocular lens 30 of the three-lobed haptic design wherein a lens optic 32 is made of a hydrogel material as described above with haptics 34 being optionally made of a hydrogel material or a non-hydrogel material. The smallest profile that this lens presents is shown as distance 35. One or more of the haptics may be folded into the center portion of the lens to reduce the cross-section in at least one dimension. FIG. 8 shows a lens of FIG. 7 where two lobes have been folded in. This configuration provides a much smaller profile 36 as compared to the configuration of FIG. 7. FIG. 9 shows such a lens where three lobes have been folded in, providing a smaller total package for insertion in the eye.

Figure 10:
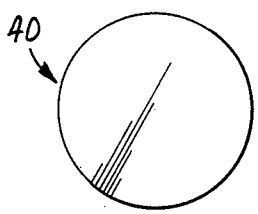
FIG. 10 shows an intraocular lens of the disc design.
Figure 11:
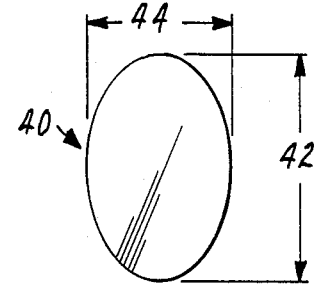
FIG. 11 shows the lens of FIG. 10 after being rolled.

FIG. 10 shows an intraocular lens 40 made in a disc design. This lens may be reconfigured so that it elongates along one dimension to the length 42 and reduces in width in the other dimension to the length 44 as shown in FIG. 11.

Figure 12:
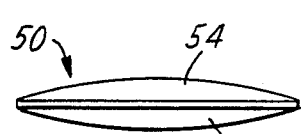
FIG. 12 shows an edge view of an intraocular lens.
Figure 13:
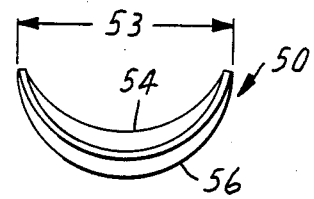
FIG. 13 shows the lens of FIG. 12 after it has been folded.

FIG. 12 shows the edge view of an intraocular lens 50 having convex surfaces 54 and 56. This lens may be folded as shown in FIG. 13, thus reducing the overall width 53 of the lens. Note that in folding, the convexity of one side of the lens 56 is increased with the other side of the lens 54 being converted to a concave configuration. The lens is then dehydrated in this folded configuration.

Figure 14:
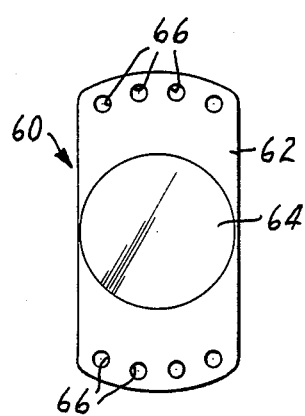
FIG. 14 shows a lens with a built-in apertures for grasping while stretching.
Figure 15:
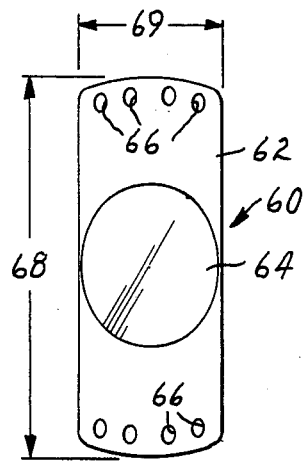
FIG. 15 shows the lens of FIG. 14 after it has been stretched.

FIG. 14 shows a modification of the disc-shaped lens 60 having an optic 64 surrounded by an annulus 62 having apertures 66 enabling the ready grasp of a stretching instrument to the lens. FIG. 15 shows a representation of the lens 60 having been stretched in one dimension, so that the overall length 68 increases while the width 69 decreases.

In the method of this invention, the lens may be reconfigured by any means which would reduce the profile of the lens in at least one dimension. The length of the profile of the reconfigured and dehydrated lens of this invention may be less than approximately 60 percent of the length of the corresponding fully hydrated lens. Preferably, the length of the profile of the reconfigured and dehydrated lens of this invention should be less than approximately 35 percent of the length of the corresponding fully hydrated lens. Most preferably, the length of the profile of the reconfigured and dehydrated lens of this invention should be less than approximately 25 percent of the length of the corresponding fully hydrated lens. The reconfiguration may be accomplished by any means, such as stretching, rolling, folding or compressing, as is appropriate for each lens depending on the capabilities of the lens material selected and the particular design embodiment of the lens.

Compressing the lens may be accomplished by inserting the lens in a vice-like clamp and applying pressure in an inward fashion. The lens will both decrease in width while elongating in length under this means of reconfiguration. Substantially the same result can be achieved by stretching the lens. In this method the two opposing sides of the lens are clamped and the clamps are pulled apart, thereby elongating the lens in one dimension and reducing the width in the other dimension. Through this operation, the lens narrows in width in a manner analogous to the stretching of a rubber band. Apertures can be placed in the annulus of a disc-shaped lens to assist in clamping the edges of the lens of this design.

A lens may be rolled by inserting the lens in a glass funnel and forcing the lens into the stem portion of the funnel by use of a plunger or by hydraulic pressure. The lens takes a rolled appearance in conforming to the shape of the funnel and simply drops out of the lens when dehydrated due to shrinkage.

A lens may be folded by use of a mechanical clamp such as shown in FIG. 50 of U.S. Pat. No. 4,573,998, incorporated herein by reference. Pressure is applied to the edges of the lens so that it folds using care that the lens is not creased or damaged in this process so that it will rehydrate to an optically correct lens.

The haptics are optionally compressed or drawn in a radially inward fashion to positions generally in a plane perpendicular to the visual axis of the lens in front or in back of the optic in order to reduce the total distance between the radially outermost points of the haptics. Said haptics are optimally compressed or drawn inwardly in such a manner that the haptics are not folded over or twisted in any way. The haptics in this step should travel in a generally direct line without rotation of the haptic relative to the optic, and will follow the same direct path upon rehydration. When following this careful reconfiguration of the haptics, the radially outermost points continue to be located on the radially outermost surface of the haptic. The possibility of damage to fragile ocular tissues is thereby reduced which could otherwise be caused by the sweeping out of an arc that would result if the haptics were simply folded over to the same position.

The haptics may be compressed together by means such as a clamp or may be simply tied together. The lens is then partially or fully dehydrated in this position. The physical reconfiguration of the haptics in this manner reduces the length of the lens while the shrinkage from dehydration reduces the overall size of the lens, presenting a lens that is more easily placed inside the capsular bag than lenses that have not been reconfigured and dehydrated.

When the haptics are made from a hydrogel material, they tend to expand or swell more quickly than the optic of the lens because the optic is generally relatively thicker than the haptic. This more rapid expansion provides for relatively rapid placement and stabilization of the lens in the eye, even before complete rehydration of the lens.

The lens to be used in this process should meet prescribed shape, dimension and physical characteristics, so that it can endure the physical stress placed on it by this method and return to an undamaged configuration, providing an optically correct lens.

The shape and dimension of the lens is dictated by various design requirements in creating an optically correct lens and by the preferences of the physician. The lens generally consists of an optic and may include a supporting structure which may, for example, be one or more haptics, handles or extensions for ease of handling the lens or may be an annulus surrounding the optic. Intraocular lenses are currently available in many design embodiments, which are typically formed by milling the prescribed shape from xerogel (fully dehydrated hydrogel) pellets. These designs could also optionally be moulded. One such design is the disc haptic, which is an optic surrounded by non-refractive annulus to provide support. Another design is the three-lobed haptic design, which haptics are typically milled out from a dry disc haptic design. A third design consists of C-shaped haptics extending from the optic, which haptics are also typically milled out from the disc haptic design. A fourth design is the J-haptic design, which comprises J-shaped haptics extending out from the optic. All of the above haptics may optionally be composed of a different material than the optic, and may extend from the optic at an angle rising out of the plane perpendicular to the optic visual axis. A shorthand name for these designs may be provided by quickly describing the physical attributes of the lens. Thus, a three-lobed haptic where the haptics are in the same plane as the optic (the plane perpendicular to the visual axis and dividing the thickest portion of the lens) would be known as a 3-planar design. The same lens where the haptics are rising 10 degrees off of the plane described above would be a 3-10 degree lens. Similarly, a lens having two C-shaped haptics in the same plane as the optic would be a C-planar design, and so on.

In carrying out the method of this invention, substantial reductions in effective profiles of the lens may be achieved, as reflected in table below delineating observed reductions in the diameters of the lens.

TABLE 1

| # | LENS (constructed from PVA material) | DIAMETER (mm) |
|---|---|---|
| 1 | 3-10° hydrated | 9.5 |
| 2 | 3-10° dehydrated | 8.0 |
| 3 | 3-10° dehydrated (one lobe folded) | 5.4 |
| 4 | 3-10° dehydrated (two lobes folded) | 4.7 |
| 5 | 3-planar hydrated | 9.5 |
| 6 | 3-planar dehydrated | 7.8 |
| 7 | 3-planar dehydrated (three lobes folded as shown in FIG. 8) | 4.8 |
| 8 | 3-planar dehydrated (rolled) | 2.8 |
| 9 | C-planar hydrated | 9.5 |
| 10 | C-planar dehydrated | 8.0 |
| 11 | C-planar dehydrated (rolled) | 2.7 |

TABLE 1-continued

| # | LENS (constructed from PVA material) | DIAMETER (mm) |
|---|---|---|
| 12 | Disc hydrated | 10.5 |
| 13 | Disc dehydrated | 8-8.2 |
| 14 | Disc dehydrated (rolled as shown in FIG. 13) | 2.7 |

The lens may be initially prepared with the subsequent reconfiguration of the lens in mind. Thus, a predictable stress placed on the lens which would change the optics of the lens after rehydration may be compensated for in the initial preparation of the lens. For example, one could prepare a xerogel which would have improper optics after hydration without reconfiguration, but which after reconfiguration and rehydration would exhibit proper optics due to the change in optical properties caused by the predicted stresses to the material.

With regard to physical characteristics, the lens material should possess sufficient resiliency that it does not permanently stretch or crack. Furthermore, the phenomenon of irreversible or permanent reconfiguration must not occur, or the material will not recover its shape upon rehydration in the eye. A more fragile or less elastic hydrogel might perform adequately in a reconfigured lens design involving a relatively low degree of reconfiguration. For example, a rolled lens configuration, where the lens is reconfigured into a roughly cylindrical shape before drying, would probably be the least demanding reconfiguration because it has no sharp corners or bends. The radius of curvature of the shape could be enlarged until the point where the material would survive the reconfiguration. A less fragile or more elastic material, such as the PVA material disclosed below, could withstand a much greater degree of reconfiguration.

Elongation is a measurement of the relative mechanical properties of a material, and is an indication of the capacity of materials to withstand the reconfigurations of this invention. The measurement may be acquired by performing a test in accordance with ASTM D412-80. A commercially available tensile tester may be modified to accept sample rings rather than strips. The rings may be held over pegs on a sample holder rather than in conventional jaws, with the object of avoiding sample slippage. Measurements should be carried out with samples immersed in water to prevent drying of the samples during testing.

The lens materials should exhibit a capacity to elongate without breaking to withstand the stresses of certain reconfigurations. Preferred materials should show elongation of 50 percent or more, such as possessed by the hydrogel of polyhydroxy methyl methacrylate and most preferred materials will show an elongation of greater than 100 percent, such as the hydrogel derived from poly(vinyl trifluoroacetate).

For example, regions of a lens having thicknesses of about 0.1-0.2 mm, e.g., hydrogel haptics, when folded 180 degrees will experience an elongation along the outside surface of such a fold which is equivalent to about 1.5 times the unfolded state. Thus, a material used in a reconfigured lens requiring bending or folding of this type must have an elongation-at-break or ultimate elongation of at least 50 percent when tested in a conventional stress-strain tensile test in the hydrated state. As the lens element to be reconfigured becomes thicker, the elongation along such outermost surfaces of folds or bends becomes greater, and thus the folding of thick elements of a lens requires materials having ultimate elongation values greater than the about 50 percent level, and will need ultimate elongations of up to 100 percent or greater depending on the thickness and the extent of folding chosen. The lens material and its physical characteristics must be considered along with the configuration of the reconfigured lens in order to have a successful process/result. For the most extreme distortions, a lens material having very high elongation values is needed, such as the PVA hydrogel material described below, which displays ultimate elongations of 1000 percent or greater. Such a material can be reconfigured in any of the ways described in this application without failure or breakage due to the unusually high ultimate elongation of the material.

The material should also contain sufficient water content so that the lens will increase in tensile strength upon dehydration sufficiently so as to maintain its reduced profile configuration and will also reduce in size or "shrink." It should be noted that an absolute dehydration of the lens is not necessarily required. A partial dehydration of the lens is contemplated, provided that the lens will maintain its modified configuration. Thus, the lens may be dehydrated to within 10 percent of total dehydration, or even 20 percent of total dehydration provided that it maintains at least some degree of the reduced profile configuration. The lens should be sufficiently dehydrated so that the modified lens will not relax or partially lose its shape over a reasonable storage period while in the dehydrated state. Percentage of relaxation is defined as the ratio of absolute distance traveled by a reconfigured lens member from its reconfigured and dehydrated state as compared to the distance of the member as between an unmodified dehydrated lens and a fully reconfigured and dehydrated lens. For example, a lens should not relax more than 5 percent over a three month period. Optimally, the lens should not relax more than 2 percent over a three month period. The optional storage of the lens in a humidity controlled environment is contemplated to assist to this end.

The lens element material may be of any well known material typically used in the manufacture of lens elements, provided that it meets the above recited physical requirements. Examples of such materials include homopolymers and copolymers of acrylate and methacrylate esters having at least one hydroxyl group on the side chain, such as 2-hydroxyethyl methacrylate, ethylene glycol dimethacrylate, hydroxyethoxyethyl methacrylate, hydroxydiethoxy methacrylate, and glyceryl methacrylate, as well polymers and copolymers of monomers such as methoxyethoxyethyl methacrylate, methoxydiethoxyethyl methacrylate, methoxyethyl methacrylate, methacrylate acid, vinyl alcohol, vinyl acetate, and N-vinyl-2-pyrrolidone and related N-alkenyl-2-pyrrolidones. Examples of useful hydrogels are disclosed in U.S. Pat. No. 4,664,666, issued to Barrett, incorporated herein by reference. Other useful hydrogels are disclosed in Wichterle, "Hydrogels," *Encyclopedia of Polymer Science and Technology*, New York, Interscience, 1971, pp. 273-290; Wichterle et al., "Hydrophilic Gels for Biological Use," *Nature*, 185: 117-118, 1960; and Ratner et al., "Synthetic Hydrogels for Biomedical Applications," *Hydrogels for Medical and Related Applications*, American Chemical Society, Washington, D.C., 1976, pp. 1-35; the disclosures of which are incorporated herein by reference. Cross-linked hydrogels are also useful in accordance with the present invention. For example, poly(hydroxyethyl methacrylate) cross-linked with 31 percent ethylene dimethacrylate is a preferable cross-linked hydrogel. Other cross-linked hydrogels are disclosed in European Patent Application No. 188,110, which corresponds to U.S. Ser. No. 809,933. Miscible blended hydrogel materials as described in U.S. Pat. No. 4,771,089, incorporated herein by reference, provide good refractive indices and are also useful materials which may be selected for use in this invention.

Particularly preferred hydrogel polymers for use in this invention are derived from poly(vinyl trifluoroacetate) copolymers (PVA) such as disclosed in U.S. Pat. No. 4,618,649 and U.S. Pat. No. 4,693,939, each issued to Ofstead, incorporated herein by reference.

The hydrogel polymer may also contain a UV absorbing monomer such as are known in the intraocular lens art, as disclosed, for example, in U.S. Pat. Nos. 4,310,650 and 4,177,122, both incorporated herein by reference.

The lens prepared of this material may optionally contain one or more haptics made of the same or different material to assist in positioning, affixing or stabilizing the lens in the eye, for ease of handling in the insertion procedure or for assistance in reconfiguring the lens before dehydration. Haptics may alternatively be prepared from materials such as nylon, polyurethane, silicone, polyamide, polypropylene, polyimide, polyvinylidene fluoride and polyethylene.

Dehydration is achieved by any appropriate method, such as passing air or nitrogen over the lens, allowing the lens to air dry or placing the lens in a dry environment such as in the presence of a desiccant. This dehydration may optionally be localized to a particular portion of the lens or may encompass the entire lens.

In the use of the lens of the present invention, the physician will remove the natural lens through phacoemulsification techniques and insert the dehydrated and reconfigured lens in the eye through a relatively small incision. A relatively small incision may be defined as an incision which is smaller than the diameter of the natural lens. Typically, these incisions are in the range of about 2 to 5 mm. The lens is placed in the capsular bag where it will rehydrate using the natural fluids of the eye. This rehydration takes place to an extent sufficient to provide stabilization in the eye in about 1 minute to about 20 minutes. Optimally, the rehydration will take place within about 5 minutes. This rehydration process is a controlled expansion of the lens and is achieved without sudden recoil of the lens and without the physical damage fragile eye parts that such a recoil could cause. The lens generally fully rehydrates to provide proper optics in about 24 hours.

The artificial intraocular lens of this invention may optionally be positioned in the posterior or anterior chambers of the eye. Most preferably, a lens containing compressed haptics is inserted in the capsular bag so that the haptics are generally in the plane on the opposite side of the optic from the incision in the capsular bag so as to minimize the possibility of expansion of the haptic through the incision to a position outside of the bag.

The methods of this invention may be more fully understood by reference to the non-limiting examples described below.

EXAMPLE 1—PREPARATION OF COPOLYMER OF VINYLTRIFLUOROACETATE

A copolymer is prepared by the method of U.S. Pat. No. 4,673,539 to Hammar, et al, example 27.

EXAMPLE 2—LENS BUTTONS FROM COPOLYMER OF EXAMPLE 1

The solid copolymer from example 1 is thoroughly dried by passing a stream of dry nitrogen over the material, and material is then placed in a mold cavity of cylindrical shape having a diameter of about 6 mm. and a depth of about 2.5 mm. The mold is closed and heated in a press to about 200° C. for approximately 3 minutes, and then cooled to give the molded parts, which are discs or lens buttons used for lathing procedures.

EXAMPLE 3—LENS LATHING

An intraocular lens of the disc haptic (planar disc) type as shown in FIG. 10 is lathed to give a 6.0 mm optical zone and an overall diameter of 11.0 mm, with the disc haptic thickness of about 0.26 mm. This planar disc haptic lens is used as is for making xerogel lenses having the planar disc configuration, and is also used as the basic shape for machining or milling operations to make other haptic designs.

EXAMPLE 4—HAPTIC MILLING—THREE-LOBED HAPTIC DESIGN

Planar disc haptic lens of example 3 is placed in a vacuum holding fixture in a micromilling machine and the mill is operated in such a way as to cut material from the disc haptic region to leave the three-lobed haptic design of FIG. 7.

EXAMPLE 5—HAPTIC MILLING—C-SHAPED HAPTIC DESIGN

A planar disc haptic lens of example 3 is placed in a vacuum fixture in a micromilling machine and the mill is operated in such a way as to cut material from the disc haptic region to leave the C-shaped haptic design of FIG. 1.

EXAMPLE 6—SOLVOLYSIS OF LATHED/MILLED LENSES

The lenses of examples 3, 4, 5, etc. are placed in a container with approximately 5 ml. of methanolic ammonium hydroxide solution prepared by mixing 90 parts methanol with 10 parts concentrated ammonium hydroxide. The solvolysis reaction is allowed to proceed overnight and the lenses are then removed and placed in distilled water to wash and hydrate. The distilled water is changed repeatedly to remove any soluble materials, resulting in hydrated intraocular hydrogel lenses ready for further processing according to this invention. (This hydrogel material as prepared in these examples has a tensile strength of about 2000 psi, or 140 kg/cm2, and elongation at break of about 1000 percent.)

EXAMPLE 7—PREPARATION OF ROLLED LENS

Hydrogel lenses of either disc, 3-lobed, or C-shaped haptic designs are slid into a glass tube having an inside diameter of approximately 3.0 mm. and a slow flow of nitrogen gas is allowed to flow through the tube overnight. The lens is dried in the constrained curved or rolled shape and undergoes enough shrinkage to actually slide out of the glass tube easily. The lenses prepared in this way are placed in glass vials and kept at room temperature and ambient humidity until evaluation in experimental animals; no tendency to unroll or resume the original shape is noted during this storage, i.e., the rolled lenses retain the rolled shape very well. Curved lenses had a diameter (of the "cylinder") of about 2.7 mm, which allows the surgical placement of the lenses through an extremely small incision.

EXAMPLE 8—PREPARATION OF FOLDED HAPTIC LENSES

Hydrated hydrogel lenses of the 3-lobed design are subjected to haptic folding techniques as follows: one lens is clamped so that one-haptic is folded against the optic surface and is allowed to dry in that configuration. A second lens is clamped so that two-haptics are folded against the optic surface and is allowed to dry in that configuration. A third lens has all three-haptic reconfigured toward the center of the optic zone by fastening the haptics with a length of fine thread and allowing drying to occur. The dried dimensions of the three dry lenses (measured to ascertain the length of the surgical incision which would be needed to allow placement in eye) are 5.4, 4.7, and 4.8 mm respectively. This should be compared with the approximately 9.5 mm dimension of the lenses in the hydrated unfolded state.

We claim:

1. A method of preparing an artificial intraocular lens for implantation within the eye comprising the steps of:
   (a) providing an intraocular lens which consists of an optic and at least one haptic, both made of the same hydrogel material which material Las prescribed shape, dimension and physical characteristics such that it can be
      (i) folded, stretched, rolled, compressed or otherwise reconfigured to a configuration such that the profile of the lens is reduced in at least one dimension,
      (ii) dehydrated so that the lens will substantially retain the configuration which provides the reduced profile,
      (iii) inserted through a relatively small incision made in the ocular tissue, and
      (iv) allowed to rehydrate by the natural fluid present in the eye and expand to provide an optically correct lens, wherein the haptic is oriented radially outward in a conventional haptic position;
   (b) applying force to the haptic or haptics radially inward so that the haptics are reconfigured to a position in front of or in back of the optic of the lens; and
   (c) dehydrating the lens sufficiently so that the haptic or haptics substantially retain their position.

2. The method of claim 1 wherein the lens contains two opposingly located haptics.

3. The method of claim 1 which additionally comprises the step of stretching, folding, rolling or compressing the partially dehydrated lens, thereby further reducing the profile of the lens in one dimension, and further dehydrating the lens so that it substantially retains the configuration providing a reduced profile.

4. The method of claim 1 wherein the haptic or haptics are compressed or drawn radially inward in a generally direct line and without rotation of the haptic relative to the optic to positions generally in a plane perpendicular to the visual axis of the lens and in front of the optic of the lens.

5. The method of claim 1 wherein the haptic or haptics are compressed or drawn radially inward in a generally direct line and without rotation of the haptic relative to the optic to positions generally in a plane perpendicular to the visual axis of the lens and in back of the optic of the lens.

6. A method of preparing an artificial intraocular lens for implantation within the eye comprising the steps of:
   (a) providing an intraocular lens which consists of an optic made of a hydrogel material, which hydrogel material has prescribed shape, dimension and physical characteristics such that it can be
      (i) folded, stretched, rolled, compressed or otherwise reconfigured to a configuration such that the profile of the lens is reduced in at least one dimension,
      (ii) dehydrated so that the lens will substantially retain the configuration which provides the reduced profile,
      (iii) inserted through a relatively small incision made in the ocular tissue, and
      (iv) allowed to rehydrate by the natural fluid present in the eye and expand to provide an optically correct lens, and at least one haptic made of non-hydrogel material, wherein the haptic is oriented radially outward in a conventional haptic position;
   (b) applying force to the haptic or haptics radially inward so that the haptics are relocated to a position in front of or in back of above the optic of the lens; and
   (c) dehydrating the lens sufficiently so that the haptic or haptics substantially retain their position.

7. The method of claim 6 wherein the lens contains two opposingly located haptics.

8. The method of claim 6 which additionally comprises the step of stretching, folding, rolling or compressing the partially dehydrated optic, thereby further reducing the profile of the lens, and further dehydrating the lens so that it substantially retains the configuration providing a reduced profile.

9. The method of claim 6 wherein the haptic or haptics are compressed or drawn radially inward in a generally direct line and without rotation of the haptic relative to the optic to positions generally in a plane perpendicular to the visual axis of the lens and in front of the optic of the lens.

10. The method of claim 6 wherein the haptic or haptics are compressed or drawn radially inward in a generally direct line and without rotation of the haptic relative to the optic to positions generally in a plane perpendicular to the visual axis of the lens and in back of the optic of the lens.

* * * * *

UNITED STATES PATENT AND TRADEMARK OFFICE
CERTIFICATE OF CORRECTION

PATENT NO. : 4,919,662

DATED : April 24, 1990

INVENTOR(S) : Randall L. Knoll et al.

It is certified that error appears in the above-identified patent and that said Letters Patent is hereby corrected as shown below:

Col. 11, line 34, delete "Las" and insert -- has -- therefor.

Signed and Sealed this

Twenty-ninth Day of October, 1991

Attest:

HARRY F. MANBECK, JR.

Attesting Officer          Commissioner of Patents and Trademarks